United States Patent
Aurich et al.

(10) Patent No.: US 11,597,952 B2
(45) Date of Patent: Mar. 7, 2023

(54) METHOD FOR THE PRODUCTION OF CARBOXYLIC ACIDS UNDER UNSTERILE CONDITIONS

(71) Applicant: HELMHOLTZ-ZENTRUM FÜR UMWELTFORSCHUNG GMBH-UFZ, Leipzig (DE)

(72) Inventors: Andreas Aurich, Leipzig (DE); Steffi Hunger, Machern (DE); Mi-Yong Becker, Leipzig (DE); Norbert Kohlheb, Leipzig (DE); Roland Arno Müller, Markranstädt (DE)

(73) Assignee: HELMHOLTZ-ZENTRUM FÜR UMWELTFORSCHUNG GMBH—UFZ, Leipzig (DE)

( * ) Notice: Subject to any disclaimer, the term of this patent is extended or adjusted under 35 U.S.C. 154(b) by 147 days.

(21) Appl. No.: 16/624,868

(22) PCT Filed: Jun. 23, 2017

(86) PCT No.: PCT/EP2017/065589
§ 371 (c)(1),
(2) Date: Dec. 19, 2019

(87) PCT Pub. No.: WO2018/233851
PCT Pub. Date: Dec. 27, 2018

(65) Prior Publication Data
US 2020/0131543 A1  Apr. 30, 2020

(51) Int. Cl.
*C12P 7/48* (2006.01)
*C12N 1/16* (2006.01)

(52) U.S. Cl.
CPC ........... *C12P 7/48* (2013.01); *C12N 1/16* (2013.01); *C12N 2500/60* (2013.01); *C12N 2500/70* (2013.01)

(58) Field of Classification Search
CPC ...... C12P 7/48; C12P 7/44; C12P 7/40; C12P 7/42; C12N 1/16; C12N 2500/60; C12N 2500/70
See application file for complete search history.

(56) References Cited

U.S. PATENT DOCUMENTS

2017/0183670 A1* 6/2017 Stephanopoulos et al. ................. C12N 15/81

FOREIGN PATENT DOCUMENTS

DE  102004028179 B4 * 12/2006 ................ C12P 7/44

OTHER PUBLICATIONS

Aurich et al., DE102004028179B4—English Machine translation PTO; "Process for the biotechnological preparation of functionalized di-and tricarboxylic acids", Published on Dec. 14, 2006 (total pages with English Machine translation 1-12). (Year: 2006).*
Barth et al., "Physiology and genetics of the dimorphic fungus *Yarrowia lipolytica*", FEMS Microbiology Reviews, 1997, vol. 19, pp. 219-237. (Year: 1997).*
International Search Report and Written Opinion of corresponding PCT/EP2017/065589, dated Mar. 8, 2018, 18 pages.
Kamzolova et al, "Lipase Secretion and Citric Acid Production in *Yarrowia lipolytica* Yeast Grown on Animal and Vegetable Fat", Food Technology and Biotechnology, vol. 43, No. 2, Sep. 12, 2004 (Sep. 12, 2004), p. 113-122.
Watanabe et al, "Fermentative L-(+)-lactic acid production from non-sterilized rice washing drainage containing rice bran by a newly isolated lactic acid bacteria without any additions of nutrients", Journal of Bioscience and Bioengineering, vol. 115, No. 4, Apr. 2013 (Apr. 2013), p. 449-452.
Chi et al, "Lipid Production by Culturing Oleaginous Yeast and Algae with Food Waste and Municipal Wastewater in an Integrated Process", Applied Biochemistry and Biotechnology; Part A: Enzyme Engineering and Biotechnology, Humana Press Inc, New York, vol. 165, No. 2, May 13, 2011 (May 13, 2011), p. 442-453.
Santamauro et al, "Low-cost lipid production by an oleaginous yeast cultured in non-sterile conditions using model waste resources", Biotechnology for Biofuels, Biomed Central Ltd, GB, vol. 7, No. 34, Mar. 4, 2014 (Mar. 4, 2014), p. 1-11.
Taskin et al, "Microbial lipid production by cold-adapted oleaginous yeast *Yarrowia lipolytica* B9 in non-sterile whey medium", Biofuels, Bioproducts & Biorefining, vol. 9, No. 5, Apr. 17, 2015 (Apr. 17, 2015), p. 595-605.
Sarris et al, "Production of added-value metabolites by *Yarrowia lipolytica* growing in olive mill wastewater-based media under aseptic and non-aseptic conditions", Engineering in Life Sciences, vol. 17, No. 6, Mar. 13, 2017 (Mar. 13, 2017), p. 695-709.

* cited by examiner

Primary Examiner — Satyendra K Singh
(74) Attorney, Agent, or Firm — Lewis Roca Rothgerber Christie LLP

(57) ABSTRACT

The aim of the invention is to provide a method for biotechnological production of carboxylic acids, in which the acid-forming micro-organisms are cultured in an unsterile manner in a submerged phase containing waste water containing all carbon and nutrient medium components necessary for the production of the carboxylic acid, which method avoids the disadvantages of known methods and enables high product concentrations and productivity while at the same time the resources of water and power are being conserved. This aim is achieved, according to the invention, in that micro-organisms are used that are cultured under unsterile conditions in a culture medium containing waste water with the addition of carbon-rich compounds.

18 Claims, No Drawings

METHOD FOR THE PRODUCTION OF CARBOXYLIC ACIDS UNDER UNSTERILE CONDITIONS

CROSS-REFERENCE TO RELATED APPLICATION(S)

This application is a U.S. National Phase Patent Application and claims priority to International Application Number PCT/EP2017/065589, filed on Jun. 23, 2017, the entire contents of which are incorporated herein by reference.

The invention relates to a method for the biotechnological production of carboxylic acids.

It is known that through the cultivation of bacteria, yeasts and filamentous fungi, a large number of mono-, di- and tricarboxylic acids such as malic acid, succinic acid, pyruvic acid, citric acid, fumaric acid, gluconic acid, itaconic acid, ketoglutaric acid or lactic acid can be obtained in high product concentrations, product formation rates, selectivities and yields. These carboxylic acids are available for a large number of applications in various branches of industry (such as the chemical, food and pharmaceutical sectors).

Here, carbohydrates, proteins and lipids from renewable raw materials and waste products that contain these substrate classes are mainly used as carbon sources for growth and the formation of the carboxylic acid of the micro-organisms. Here, the use of carbon sources from agricultural farming for biotechnological procedures often competes with their use as food and fodder.

In order to achieve high productivity figures, the biotechnological production methods for carboxylic acids are almost entirely implemented with the maintenance of the generally known sterile (aseptic) cultivation conditions, wherein in particular, the carbon sources, culture media components, the required air feed and the reactor equipment for conducting the bioproduction stage are subjected to corresponding measures (such as chemical or thermal sterilisation, filters) for the creation and maintenance of sterile conditions.

The biotechnological production methods, which are mainly conducted as submersion cultivations, require the provision of considerable quantities of fresh process water, frequently of drinking water quality and qualities that exceed this level. After completing the cultivations and the separation of the biomasses and carboxylic acids, the remaining process water must usually be fed to a convention waste water treatment system.

A particularly high proportion of biotechnologically produced carboxylic acids is accounted for by citric acid (2-hydroxy propane-1,2,3-tricarboxylic acid), with annual global production of 1.6 million tonnes. Due to its taste, antioxidant, colour stabilising and complex-forming properties, it is known that citric acid is widely used in the chemical industry (e.g. as a detergent and cleaning agent additive, decalcifier), the food and drinks industry (e.g. taste enhancement) and in the pharmaceutical industry (e.g. stabilisation of stored blood).

The submersion procedure with the filamentous fungus *Aspergillus niger* has been established for decades as an industrial production method for citric acid. Here, only carbohydrates such as saccharose, glucose, starch hydrolysates and waste products containing carbohydrates are used as carbon sources, in particular cane sugar and beet molasses.

Despite decades of optimisation of the *Aspergillus* process, this process has a series of disadvantages. A particular disadvantage for all submersion methods for obtaining citrate is the entirely sterile process required, in which the sterilisation (110-130° C. for 0.5-1 h) or pasteurisation (85-95° C.) of the carbon sources and sterile filtration of the air is involved for the provision of oxygen for the fungi cultures. For this purpose, considerable amounts of expenditure for energy and apparatus are required.

A further disadvantage with submersed citrate production with *Aspergillus niger* are the high purity standards regarding the process water for cultivation. As a minimum, drinking water quality should be used.

In addition, the low tolerance of *Aspergillus niger* with regard to heavy metals requires its prior precipitation from the substrates and process waters used through the addition of cyanides (e.g. hexacyanoferrate) before the bioprocess stage.

Yeast-based methods for obtaining citric acid have been, and are still being, developed since the 1960s, as an alternative to the *Aspergillus niger* method.

Here, mainly the yeast type Yarrowia lipolytica was used, which stands out for its wide variety of suitable carbon sources for the formation of citric acid, and which thus overcomes the disadvantage of the narrow suitable substrate spectrum that characterizes Aspergiflus niger.

The cultivations with *Y. lipolytica* are generally achieved under entirely sterile conditions (including sterile carbon sources and ventilation) and are preferably realised in batch, fedbatch or semi-continuous operation.

The disadvantage for all genetically modified *Y. lipolytica* yeast strains is that their use is subject to the conditions of the German genetic technology act (GenTG), as well as comparable international regulations, and thus explicitly requires a sterile process completion in closed systems, which prevents the GMO from escaping into the environment.

Yeast-based methods for citrate formation with *Y. lipolytica*, unlike the *A. niger* methods, are usually conducted using process water of at least drinking water quality.

The object that forms the basis of the invention consists of avoiding the disadvantages of the existing methods for the biotechnological production of carboxylic acids and to provide such methods that enable high product concentrations and productivities with simultaneous protection of water and power as resources.

The object is attained with the invention in accordance with Claim 1; the subclaims are preferred variants.

According to the invention, a submerged method for the biotechnological production of carboxylic acids with micro-organisms is provided, wherein the micro-organisms are cultured in an unsterile manner in a waste water, with the addition of carbon-rich compounds.

Preferably, the term "carboxylic acids" in the invention refers to the intermediates of the tricarboxylic acid cycle: aconitic, malic, succinic, citric, fumaric, isocitric, a-ketoglutaric, oxaloacetic acid and the pyruvic and itaconic acid compounds associated with the tricarboxylic acid cycle. In a particularly preferred manner, the citric acids and their salts (e.g. calcium, potassium and sodium citrates) are identified.

The term "micro-organisms" comprises algae, bacteria, filamentous fungi and yeasts. Preferably, the term "yeasts" refers to all types of the genuses Candida, Cryptococcus, Debaromyces, Hansenula, Meyerozyma, Pichia, Pseudozyma, Rhodosporidium, Rhodotorola, Schizosacchoromyces, Saccharomyzes, Torulopsis and Yarrowia. In a particularly preferred manner, the yeast type is Yarrowia lipolytica. In a very particularly preferred manner, the strain Yarrowia lipolytica H181 (DSM 7806) is used, which is stored at the Deutsche Sammlung von Mikroorganismen und Zellkulturen GmbH under the label DSM 7806. The Deutsche Sammlung von Mikroorganismen und Zellkulturen GmbH is located at the DSMZ German Collection of Microorganisms and Cell Cultures, Inhoffenstr. 7B, 38124 Braunschweig. The Yarrowia lipolytica H181 strain was transferred to the Deutsche Sammlung von Mikroorganismen und Zellkulturen GmbH on Nov. 30, 1993, and the deposit was extended on Jun. 4, 2004 by a further 21 years until Oct. 25, 2034. The Yarrowia lipolytica H181 strain is registered as DSM 7806.

The term "waste water" refers to all waters that are contaminated through their use and consumption. Preferably, the use of grey water, industrial (e.g. from the food industry, the chemical, pharmaceutical and biotechnology industry, natural gas and crude oil extraction and processing) and municipal waste waters is provided.

In a particularly preferred manner, waste waters from the food processing industry (e.g. purification waters from kitchen and catering operations) and municipal waste waters after preliminary clarification are provided.

The term "carbon-rich compound" as it is used here refers to organic substrates containing carbons, which are utilised by micro-organisms as heterotrophic carbon sources. These compounds containing carbon are obtained through agricultural production or are mainly biogenic waste products. The proportion of usable carbon is here dependent on the degree of purity and preparation of the substrates. Preferably, carbon-rich compounds from agricultural production or in the form of waste products are used, which contain mono-, di-, triglycerides, fatty acids, fatty acid methyl or ethyl esters, ethanol, methanol, glycerol, glucose, fructose, galactose, lactose, lactic acid, saccharose, xylose, arabinose and/or n-alkanes (n-paraffin).

In a particularly preferred manner, the use of waste products in the form of used deep-frying oils (old deep-frying oil) containing mono-, di-, triglycerides and fatty acids, is provided.

The carbon-rich compounds used can here already be partially or fully present in the waste water when it is created, or be added in full to the waste water. Equally, mixtures of two or more carbon-rich compounds can be used for the invention.

The term "unsterile" refers to the fact that before, during and after cultivation, no usual, known measures (e.g. chemical or thermal sterilisation, pasteurisation) and devices (e.g. sterile filters for ventilation, sterile sample removal) for the production and maintenance of a germ-free and sterile state and for the prevention of the penetration of external germs into the culture medium.

The invention will be described in detail below with reference to the yeast-based biotechnological preparation of citric acid which is produced in a particularly preferred manner, without restricting it to such a method.

*Candida*, *Meyerozyma* and *Yarrowia* have been shown to be preferred yeast genuses with the ability to accumulate citric acid in high concentrations. In particular, mutants, selectants and recombinant strains of the yeast type *Yarrowia lipolytica* have the ability for citrate production with a selectivity of greater than 90%, wherein isocitric acid occurs as the sole significant ancillary product.

According to the invention, preferably *Yarrowia lipolytica* strains, preferably *Y. lipolytica* H181 (DSM 7806), are cultured under unsterile aerobic, submerged conditions in a culture medium that contains the usual, known synthetic or semi-synthetic nutrient medium components and carbon sources for the formation and precipitation of citric acid.

Here, the formation and accumulation of the citric acids is triggered in the known manner through limitation of a nutrient component (e.g. nitrogen, phosphorous or sulphur), preferably ammoniacal nitrogen. A strain-specific thiamine concentration of >0.5 mg/l thiamine×HCl., preferably 1 mg/l and up to 1,000 mg/l, is added to the culture medium.

The cultivation is implemented according to the invention preferably in such a manner that in a reaction facility, waste water is provided in unsterile form.

Preferably all reaction vessels that are suitable for submerged cultivation, but which may differ with regard to their structure, design, type of mixture and ventilation are provided as reaction facilities. Examples of reaction vessels are the usual stirring reactors, airlift reactors, bubble columns and also designs suitable for waste water treatment, such as aeration tanks or sequencing batch reactors. The reaction facilities can be designed as closed or open facilities. Open facilities mean that the penetration of micro-organisms from the environment into the reaction facility is possible.

All the necessary nutrient components and carbon-rich compounds are subsequently added in an unsterile manner to the waste water provided. Finally, the inoculating culture (inoculum) of the yeast is fed to the reaction vessel, which is produced using one or several steps in the usual, known manner. The pre-culture steps can here be conducted in a fully or partially unsterile manner.

For the invention, in principle, all types of waste water can be used that do not inhibit the growth of the *Yarrowia lipolytica*. Preferably, waste water from the cleaning stages of kitchen and catering operations, discharges from commercial oil/fat separators and from the pre-clarification stage of waste water treatment plants for communal waste waters is used. The waste waters are fed to the reaction vessel in a volume proportion of 5-100% of the entire culture medium; preferably with a proportion of 90-100%.

In principle all compounds can be used for the invention as carbon-rich compounds (carbon sources) that can be digested by *Yarrowia lipolytica*. The carbon sources can be used as individual compounds or mixtures.

The use of used vegetable or animal fats or oils, particularly preferred being old deep-frying oil, is preferably provided. The carbon source is added according to known cultivation regimes, either fully, already at the start of cultivation (batch operation), or a subsequent dose of the substrate is added at certain points in time (fedbatch operation).

The old deep-frying oils are preferably provided with a concentration of 35-40 g/l in the reaction vessel, and are subsequently dosed in an unsterile manner with a usual feeding regime for final concentrations of 100-180 g/l.

In addition, it is preferably provided that the cultivation of *Y. lipolytica* is conducted in the usual batch, fedbatch, repeated fedbatch (semi-continuous) or continuous manner of operation, wherein in a particularly preferred manner, C-operation is provided.

*Y. lipolytica* is cultured with a ph value of 2.0 to 8.0 and a temperature of 5 to 45° C., preferably at ph 3.5 to 5.5 and a temperature of 26 to 33° C.

$CaCO_3$, $Ca(OH)_2$, KOH, NaOH, $Na_2CO_3$, $NaHCO_3$ are preferably suitable as neutralisation agents for establishing the PH, particularly preferably, NaOH.

The citrate formation of *Y. lipolytica* as the known aerobic bioprocess requires the feed of oxygen during cultivation, wherein the oxygen distribution in the culture medium is realised in the usual way through ventilation and circulation. According to the invention, a dissolved oxygen concentration, measured as a pO$_2$ value, is maintained in a range of pO$_2$=1% to 100%, preferably, an oxygen saturation of pO$_2$ 20% should be guaranteed.

The cultivation of *Y. lipolytica* begins with a growth phase, which usually transitions into the product formation phase for citric acid when the growth-limiting nutrient component is used up after 8 to 30 hours. Usually, the cultivation is ceased at an economic point in time with respect to productivity, e.g. with significantly decreasing or stagnating carboxylic acid formation. The overall cultivation period generally lasts for around 60 to 250 hours, depending on the quantity of the carbon source used and the selected cultivation mode (e.g. fedbatch and repeated fedbatch).

Advantageously, the method according to the invention enables citric acid concentrations of ≥210 g/l.

The culture solution obtained according to the invention, which contains the produced citric acid and the yeast biomass of *Y. lipolytica*, can then be added to the usual method of downstream processing for the product isolation and product concentration of carboxylic acids. These methods usually include a standard separation step for micro-organisms (e.g. crossflow filtration, sedimentation, filtration, centrifugation) and an isolating step for citric acid (e.g. adsorption/desorption, precipitation, electro-dialysis with bipolar membranes, Simulated Moving Bed (SMB) chromatography, reactive extraction).

The use of the method according to the invention offers significant advantages over the current prior art, which can be summarized as follows:

- Product concentrations of ≥210 g/l of citric acid lie above the yields attained using the known methods.
- The production of citric acid under entirely unsterile conditions avoids apparatus, power and material consumption that arises with the known methods for producing and maintaining sterile culture conditions.
- The intended exclusive use of waste waters for the submerged cultivation avoids the intended use of process water and higher qualities with the existing methods, as well as the apparatus, power and material consumption required for its production.
- The preferred use of waste products as carbon-rich compounds for the production of citric acid avoids the competing use of carbon sources from agricultural farming, which can be used as food or fodder.
- The production cultures can be used as free yeast cells and thus, expenditure for cell immobilization, as is in part required in the methods and publications described, is avoided.

The invention will be described in greater detail in the examples below.

EXAMPLE 1

Obtaining the Pre-Culture

The strain *Yarrowia lipolytica* H181 (DSM 7806) was cultured on a known nutrient medium suitable for yeasts (e.g. peptone yeast extract agar or reader agar) for 24 to 48 h at 30° C.

From the grown agar culture, 2 to 3 inoculation loops were seeded on 100 ml of a sterile pre-culture solution produced with distilled water with the following composition:

| NH$_4$Cl | 3.00 g/l |
|---|---|
| KH$_2$PO$_4$ | 0.70 g/l |
| MgSO$_4$ × 7H2O | 0.35 g/l |
| NaCl | 0.10 g/l |
| CaCl$_2$ × 2H2O | 0.13 g/l |
| FeSO$_4$ × 7H2O | 3.5 mg/l |
| Thiamine × HCl | 1 mg/l |
| Trace salt solution | 5 ml/l |
| Sunflower oil | 50 g/l |

The trace salt solution of the pre-culture medium had the following composition:

| CuSO$_4$ × 5H2O | 4.0 g/l |
|---|---|
| MnSO$_4$ × 5H2O | 4.0 g/l |
| ZnCl$_2$ | 2.1 g/l |
| CoSO$_4$ × 7H2O | 0.5 g/l |
| H$_3$BO$_3$ | 5.7 g/l |

The pre-culture was cultured and at ph 5-6 in 500 ml Erlenmeyer flask with baffles at 30° C. for 48 h on a shaking apparatus with a shaking frequency of 120 to 140 rpm.

Implementation of Main/Production Culture

From the pre-culture, the seeding of 30 ml of inoculum with an inoculation ratio of 1:10 in a 0.5 l stirrer reactor with 300 ml of working volume was conducted for the implementation of the unsterile, submerged main/production cultivation, wherein the terms main and production culture are used as synonyms. The production medium contained the following components:

| NH$_4$Cl | 3.00 g/l |
|---|---|
| KH$_2$PO$_4$ | 0.70 g/l |
| MgSO$_4$ × 7H2O | 0.35 g/l |
| CaCl$_2$ × 2H2O | 0.13 g/l |
| FeSO4 × 7H2O | 3.5 mg/l |
| Thiamine × HCl | 1 mg/l |
| Trace salt solution | 1 ml/l |

(Composition of the Trace Salt Solution as for the Pre-Culture)

As a carbon source, the production medium contained an old deep-frying oil, which was previously used as deep-frying oil for two days for the production of potato chips. The old deep-frying oil had the following fatty acid pattern (mass percentages):

| Myristic acid (14:0) | 5.4% |
|---|---|
| Palmitic acid (16:0) | 0.2% |
| Stearic acid (18:0) | 1.6% |
| Oleic acid (18:1; w9c) | 58.7% |
| Vaccenic acid (18:1; w7c) | 3.5% |
| Linoleic acid (18:2) | 19.6% |
| Linolenic acid (18:3) | 8.7% |
| Arachidonic acid (20:0) | 0.4% |
| Eicosenoic acid (20:1; w9c) | 0.9% |
| Other fatty acids | 1.0% |

The waste water from the discharge of an oil and fat separator of a commercial canteen and catering operation was used as the liquid phase in order to produce the production medium. The discharge of the oil/fat separator was characterized by the following waste water-related parameters:

| Parameter | |
|---|---|
| Ph | 6.3 |
| DOC | 6.7 mg $O_2$/l |
| Conductivity | 2.17 ms/cm |
| COD | 2830 mg/l |
| $BOD_5$ | 1611 mg/l |
| TOC | 954 mg/l |
| TSS | 576 mg/l |
| TN | 32 mg/l |

All nutrient medium components of the production medium were dissolved in the waste water and added in an unsterile manner to the 0.5 l stirrer reactor. The initial concentration of the old deep-frying oil in the stirrer reactor was 40 g/l and was added in an unsterile manner in fedbatch operation in stages of 20 g/l up to a final concentration of 140 g/l. The production cultures were implemented as a duplicate batch at 30° C., stirrer speed=900 rpm and a dissolved oxygen concentration of $pO_2$=50%. The dissolved oxygen concentration was regulated via a gas mixture of air/nitrogen/oxygen, wherein the ventilation of the stirrer reactors was conducted in an unsterile manner without feed and exhaust air filters, with a total gas flow of 0.5 l/min. The ph value was established at ph 5 with 20% NaOH.

In comparison, sterile double batches with a) distilled water (including all nutrient components, sterilised at 121° C. for 20 mins) instead of waste water and old deep-frying oil (pasteurised at 80° C. for 20 mins), and b) oil/fat separator discharge (including all nutrient components, sterilised at 121° C. for 20 mins) and old deep-frying oil (pasteurised at 80° C. for 20 mins) were realised.

When the nitrogen source, ammonium sulphate, was used up after 21 h, the accumulation of citric acid and isocitric acid began in the culture solutions. After 166 h, the cultivations were ended. For the unsterile batch with waste water (discharge from oil/fat separator), a carboxylic acid formation of 137 g/l citric acid and 11 g/l of the by-product isocitric acid were determined (average values from two cultivations). This corresponded to a productivity of 0.83 g/l*h. When waste water is used under sterile conditions, the product quantities of carboxylic acids were only insignificantly increased; with distilled water, the lowest concentrations of citrate were formed (Table 1).

Cultivation took place as described in example 1, wherein a waste water (discharge of oil/fat separator) was used in the main culture, which had the following composition:

| Parameter | |
|---|---|
| PH | 5.9 |
| DOC | 1.7 mg $O_2$/l |
| Conductivity | 3.0 ms/cm |
| COD | 1760 mg/l |
| $BOD_5$ | 1036 mg/l |
| TOC | 676 mg/l |
| TSS | 315 mg/l |
| TN | 29 mg/l |

The main culture was achieved as a semi-continuous cultivation (repeated feedback operation) in a 15 l stirrer reactor. Here, cycle 1 was started with 9 l of working volume, which contained 900 ml of the pre-culture of *Y. lipolytica* H181 (DSM 7806) and an initial old deep-frying oil concentration of 40 g/l. The carbon source was fed up to a summary final concentration of 120 g/l old oil.

In contrast to example 1, the ph value 5 was established with 45% NaOH, and the oxygen supply of the yeasts was realised by means of a ventilation quantity of 4 l/min with a stirrer speed of 800 rpm. The dissolved oxygen concentration for the entire cultivation was $pO_2 \leq 20\%$.

When the nitrogen source, ammonium sulphate, was used up after 20 h, the accumulation of citric acid and isocitric acid could be registered. After a culture duration of 70 h, cycle 1 of the main cultivation was ended. The volume of the culture solution was 10.5 l and contained 77 g/l of citric acid and 3.8 g/l isocitric acid. This corresponded to a productivity of 1.1 g/l*h and selectivity of 95.2% for citric acid.

Following the completion of cycle 1, 9.5 l of the culture solution were drained down to a residual volume of 1 l, and were filled in an unsterile manner with 8 l of the oil/fat separator discharge, including the nutrient medium components of the production medium. The yeast biomass of *Y. lipolytica* H181 contained in the residual volume of cycle 1 acted as an inoculum for the continuation of the cultivation in the second cultivation cycle.

In cycle 2, 150 g/l of old deep-frying oil was added to the stirrer reactor in fedbatch mode as an external source of

TABLE 1

The production of citric acid of *yarrowia lipolytica* H181 (DSM 7806) under unsterile culture conditions (average value from two identical test batches respectively)
Example 2

| Batch | Culture duration | Citric acid (g/l) | Isocitric acid (g/l) | Productivity citrate (g/l * h) | Selectivity citrate (%) |
|---|---|---|---|---|---|
| unsterile | | | | | |
| Discharge oil separator + old deep-frying oil | 166 h | 137 ± 8.5 | 11.2 ± 1.4 | 0.83 ± 0.05 | 92.4 ± 0.5 |
| sterile | | | | | |
| a.) Distilled water + old deep-frying oil | 166 h | 125 ± 4.6 | 15.2 ± 3.7 | 0.75 ± 0.03 | 89.3 ± 2.0 |
| b.) Discharge oil separator + old deep-frying oil | 166 h | 145 ± 9.6 | 14.9 ± 0.6 | 0.88 ± 0.06 | 90.7 ± 0.2 | carbon. The conditions of cycle 1 were maintained with regard to the ph value and the oxygen supply. When the nitrogen source, ammonium sulphate, was repeatedly used up after 20 h in cycle 2, the formation of citric acid and isocitric acid by the yeast *Yarrowia lipolytica* H181 began. When cycle 2 was halted after a cycle duration of 95 h, with a total cultivation time of 165 h over both cycles, the concentration of citric acid was 91 g/l, and of isocitric acid, 4.4 g/l in a 10.6 l culture solution. Thus, the productivity (0.96 g/l*h) and selectivity (95.4%) of the citrate formation in cycle 2 were almost identical to the results of cycle 1.

Overall, in both unsterile cycles, 20.1 l of culture solution could be harvested, which contained 1.7 kg of citric acid.

EXAMPLE 3

The cultivation described in example 2 was modified such that the pre-culture was also obtained with the use of a waste water (oil/fat separator discharge). In addition, in contrast to example 2, the unsterile main culture was achieved with untreated waste water from a commercial canteen and catering operation, which was introduced as an infeed into an oil/fat separator. The waste water used (oil/fat separator infeed) had the following composition:

| Parameter | |
|---|---|
| ph | 5.8 |
| DOC | 0.6 mg $O_2$/l |
| Conductivity | 2.9 ms/cm |
| COD | 5240 mg/l |
| $BOD_5$ | 1661 mg/l |
| TOC | 1095 mg/l |
| TSS | 191 mg/l |
| TN | 117 mg/l |

The main culture was conducted as fedbatch cultivation in a 15 l stirrer reactor with a 9 l initial volume. The initial old deep-frying oil concentration was 35 g/l and was increased through the continuous addition of substrate up to 175 g/l after a culture duration of 120 h. In contrast to example 2, the stirrer speed was reduced to 600 rpm. The dissolved oxygen concentration was $pO_2$>5% during cultivation.

After 21 h, the ammonium nitrogen source was used up; from this point onwards, the citrate and isocitrate began to accumulate. When the main cultivation was halted after 166 h, 181 g/l citric acid and 5.4 g/l isocitric acid could be measured in the culture broth. This corresponded to a productivity of 1.1 g/(l*h) for citric acid. The selectivity for citrate was 97%.

EXAMPLE 4

The cultivation was repeated, as described in example 2, wherein a municipal waste water (septic tank discharge) was used as the liquid phase in the main culture. The municipal waste water had the following composition:

| Parameter | |
|---|---|
| Ph | 7.2 |
| DOC | 0.76 mg $O_2$/l |
| Conductivity | 1.66 ms/cm |
| COD | 486 mg/l |
| $BOD_5$ | 287 mg/l |

-continued

| Parameter | |
|---|---|
| TOC | 163 mg/l |
| TSS | 65 mg/l |
| TN | 91 mg/l |
| E. coli | 4.6 × 10 6 MPN/100 ml |

In contrast to example 2, the unsterile main culture was conducted as fedbatch cultivation (15 l stirrer reactor with 9 l working volume). Here, old deep-frying oil was added as a carbon source up to a final concentration of 180 g/l, starting from an initial substrate concentration of 40 g/l. The cultivation was conducted at ph 5, which was set with 45% NaOH and with a stirrer speed of 600 rpm. The air gasification rate was 4 l/min. Thus, the dissolved oxygen concentrations of $pO_2$>3% could be maintained over the entire culture duration.

After the NH4-N source was used up at 21 h, during the following cultivation of 56 h, 95 g/l citric acid and 2 g/l isocitrate were formed from *Y. lipolytica* H181 (DSM 7806), corresponding to a citric acid formation rate of 1.2 g/(l*h). The continuation of the cultivation up to 189 h led to a further increase in the citric acid concentration up to 133.7 g/l. With isocitric acid measured simultaneously at 4.8 g/l, a selectivity of 96.5% could be determined for the citrate formation. The productivity for citrate was 0.71 g/(l*h) for the entire period.

At the end of cultivation, no further evidence was found of *E. coli* germs (sum parameter of pathogenic bacteria). This is an indication of the hygienic impact of the yeast-based citrate production on waste waters.

In examples 1 to 4 above, the following abbreviations are used:

Ph ph value
DOC Dissolved oxygen content
COD Chemical oxygen demand
BODs Biological oxygen demand (after 5 days)
TOC Total organic carbon
TSS Total suspended solids
TN Total nitrogen
*E. coli Escherichia coli*

The invention claimed is:

1. A method for biotechnological production of carboxylic acids, wherein the method comprises:
culturing of microorganisms under unsterile conditions in a culture medium containing waste water,
wherein the waste water comprises carbon-rich compounds and/or the method comprises adding carbon-rich compounds to the waste water,
the microorganisms comprise strains of the yeast type *Yarrowia lipolytica*,
the carboxylic acids to be produced comprise at least one substance selected from the group consisting of aconitic, malic, succinic, citric, fumaric, isocitric, α-ketoglutaric, oxaloacetic, pyruvic, and itaconic acids, and
the carbon-rich compounds comprise at least one substance selected from the group consisting of monoglycerides, diglycerides, triglycerides, fatty acids, fatty acid methyl or ethyl esters, ethanol, methanol, glycerol, glucose, fructose, galactose, lactose, lactic acid, saccharose, xylose, arabinose, and n-alkanes,
wherein the unsterile conditions comprise that before, during and after cultivation, no chemical or thermal sterilization measures and pasteurization measures are applied; and wherein the method comprises at least one pre-cultivation step for producing inoculum of the yeast *Yarrowia lipolytica* in an unsterile manner.

2. The method according to claim 1, wherein the microorganisms comprise the yeast strain *Yarrowia lipolytica* H181 (DSM 7806).

3. The method according to claim 1, wherein the waste water is a water that is contaminated through use and consumption.

4. The method according to claim 1, wherein the waste water is fed to a reaction vessel in a volume proportion of 5-100%.

5. The method according to claim 1, wherein the culturing of microorganisms is conducted in an unsterile manner and no measures and devices are provided for production and maintenance of a germ-free and sterile state and for prevention of penetration of external germs into the culture medium.

6. The method according to claim 1, wherein the culturing of microorganisms is conducted in a reaction facility comprising reaction vessels that are selected from the group consisting of stirrer reactors, airlift reactors, bubble columns, aeration tanks and sequencing batch reactors.

7. The method according to claim 1, wherein the culturing of microorganisms is conducted at a pH of 2 to 8.

8. The method according to claim 1, wherein the culturing of microorganisms is conducted at a temperature of 5 to 45° C.

9. The method according to claim 1, wherein the method comprises a step of neutralizing with an agent selected from the group consisting of $CaCO_3$, $Ca(OH)_2$, KOH, NaOH, $Na_2CO_3$, and $NaHCO_3$.

10. The method according to claim 1, wherein a dissolved oxygen concentration is set at a range of $pO2 \leq 1\%$ to 100% during the culturing of microorganisms.

11. The method according to claim 1, wherein the culturing of microorganisms is conducted as a batch, fedbatch, semi-continuous repeated fedbatch or continuous process.

12. The method according to claim 1, wherein the culturing of microorganisms takes place without prior immobilisation of the microorganisms.

13. The method according to claim 1, wherein the waste water is selected from the group consisting of grey water, industrial wastewater, municipal waste water, waste water from cleaning stages of a kitchen and catering operation, discharges from commercial oil/fat separators and discharges from a pre-clarification stage of waste water treatment plants for communal waste waters.

14. A method for biotechnological production of carboxylic acids, wherein the method comprises:
culturing of microorganisms under unsterile conditions in a culture medium containing waste water,
wherein the waste water comprises carbon-rich compounds and/or the method comprises adding carbon-rich compounds to the waste water,
wherein the unsterile conditions comprise that before, during and after cultivation, no chemical or thermal sterilization measures and pasteurization measures are applied,
the microorganisms comprise the yeast strain *Yarrowia lipolytica* H181 (DSM 7806),
the carboxylic acids to be produced comprise at least one substance selected from the group consisting of aconitic, malic, succinic, citric, fumaric, isocitric, α-ketoglutaric, oxaloacetic, pyruvic and itaconic acids, and
the carbon-rich compounds comprise at least one substance selected from the group consisting of monoglycerides, diglycerides, triglycerides, fatty acids, fatty acid methyl or ethyl esters, ethanol, methanol, glycerol, glucose, fructose, galactose, lactose, lactic acid, saccharose, xylose, arabinose, and n-alkanes; and
wherein the method comprises at least one pre-cultivation step for producing inoculum of the yeast *Yarrowia lipolytica* H181 (DSM 7806) in an unsterile manner.

15. The method according to claim 14, wherein the waste water is a water that is contaminated through use and consumption.

16. The method according to claim 14, wherein the waste water is selected from the group consisting of grey water, industrial wastewater, municipal waste water, waste water from cleaning stages of a kitchen and catering operation, discharges from commercial oil/fat separators and discharges from a pre-clarification stage of waste water treatment plants for communal waste waters.

17. The method according to claim 14, wherein the waste water is fed to a reaction vessel in a volume proportion of 5-100%.

18. The method according to claim 14, wherein the culturing of microorganisms is conducted in an unsterile manner and no measures and devices are provided for production and maintenance of a germ-free and sterile state and for prevention of penetration of external germs into the culture medium.

* * * * *